(12) United States Patent
Cozzi et al.

(10) Patent No.: US 6,177,408 B1
(45) Date of Patent: Jan. 23, 2001

(54) DISTAMYCIN DERIVATIVES, PROCESS FOR PREPARING THEM, AND THEIR USE AS ANTITUMOR AND ANTIVIRAL AGENTS

(75) Inventors: Paolo Cozzi, Milan; Italo Beria, Villamarzana; Marina Caldarelli; Maria Cristina Geroni, both of Milan; Enrico Pesenti, Monzese, all of (IT)

(73) Assignee: Pharmacia & Upjohn S.p.A., Milan (IT)

( * ) Notice: Under 35 U.S.C. 154(b), the term of this patent shall be extended for 0 days.

(21) Appl. No.: 09/147,264

(22) PCT Filed: Apr. 24, 1997

(86) PCT No.: PCT/EP97/02158

§ 371 Date: Nov. 13, 1998

§ 102(e) Date: Nov. 13, 1998

(87) PCT Pub. No.: WO97/43258

PCT Pub. Date: Nov. 20, 1997

(30) Foreign Application Priority Data

May 14, 1996 (GB) .................................................. 9610079

(51) Int. Cl.[7] ........................... C07D 207/34; C07K 5/00; A61K 31/40; A61K 38/06; A61K 38/07
(52) U.S. Cl. ................................ 514/17; 514/18; 514/19; 514/422; 514/423; 514/426; 530/331; 530/333; 548/400; 548/518; 548/530; 548/557
(58) Field of Search ................................ 514/18, 19, 408, 514/2, 422, 423, 426; 530/331, 333; 548/518, 400, 530, 557

(56) References Cited

U.S. PATENT DOCUMENTS 5,753,629 * 5/1998 Beria et al. ............................ 514/18

* cited by examiner

Primary Examiner—Christopher S. F. Low
Assistant Examiner—Anish Gupta
(74) Attorney, Agent, or Firm—Arent Fox Kintner Plotkin & Kahn, PLLC

(57) ABSTRACT

A compound which is a distamycin derivative of formula (I), wherein n is 2, 3 or 4; $R_0$ is $C_1$–$C_4$ alkyl or $C_1$–$C_3$ haloalkyl; $R_1$ and $R_2$, which may be the same or different, are each hydrogen, $C_1$–$C_4$ alkyl optionally substituted by one or more fluorine atoms, or $C_1$–$C_4$ alkoxy; X is a halogen atom; B is selected from (A, B, C, D, E, F, G, H, I, J and K); wherein $R_3$, $R_4$, $R_5$, $R_6$, $R_7$, $R_8$, and $R_9$, which may be the same or different, are each hydrogen or $C_1$–$C_4$ alkyl, and m is 0, 1, or 2; or a pharmaceutically acceptable salt thereof. Such compounds are useful as antineoplastic and antiviral agents.

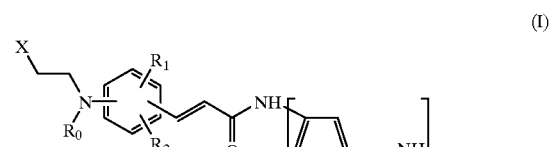

(I)

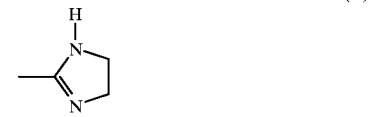

(A)

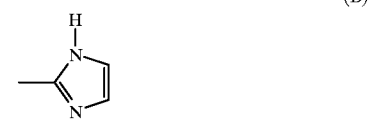

(B)

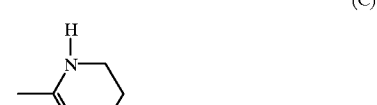

(C)

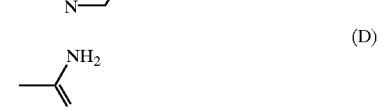

(D)

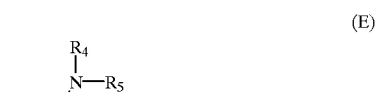

(E)

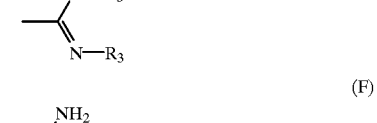

(F)

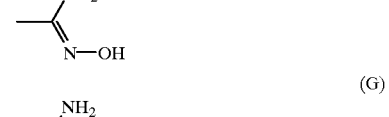

(G)

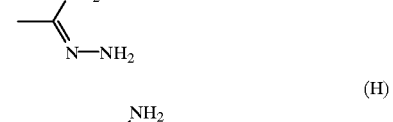

(H)

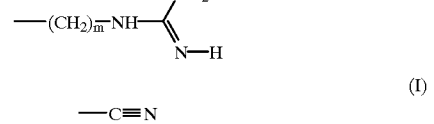

(I)

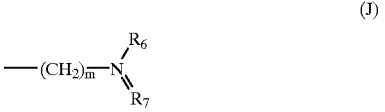

(J)

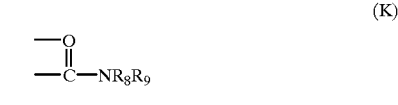

(K)

6 Claims, No Drawings

DISTAMYCIN DERIVATIVES, PROCESS FOR PREPARING THEM, AND THEIR USE AS ANTITUMOR AND ANTIVIRAL AGENTS

The present invention refers to new alkylating antitumor and antiviral agents related to the known antibiotic distamycin A:

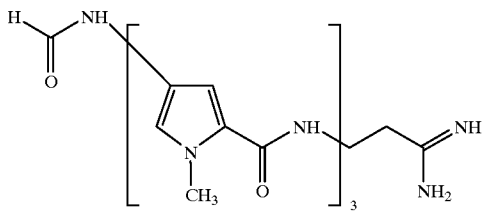

which belongs to the family of the pyrroleamidine antibiotics and is reported to interact reversibly and selectively with DNA-AT sequences interfering with both replication and transcription [Nature, 203, 1064 (1964); FEBS Letters, 7 (1970) 90; Prog.Nucleic Acids Res.Mol.Biol., 15, 285 (1975)].

DE-A-1795539 describes the preparation of distamycin derivatives in which the formyl group of distamycin is replaced by hydrogen or by the acid residue of an organic $C_1$–$C_4$ aliphatic acid or of cyclopentylpropionic acid. EP-B-246,868 describes distamycin analogues in which the distamycin formyl group is substituted by aromatic, alicyclic or heterocyclic moieties bearing alkylating groups.

It has now been found that a new class of distamycin derivatives as defined hereinunder, wherein the distamycin formyl group is substituted by an optionally alkyl and/or alkoxy substituted cinnamoyl moiety bearing as alkylating group a N-(halo)alkyl-N-haloethyl-amino group, shows valuable biological properties.

Accordingly, the present invention relates to new distamycin derivatives of formula (I) as defined hereinunder, to a process for preparing them, to pharmaceutical compositions containing them and to their use in therapy, particularly as antitumor and antiviral agents.

Therefore, object of the present invention are compounds of formula:

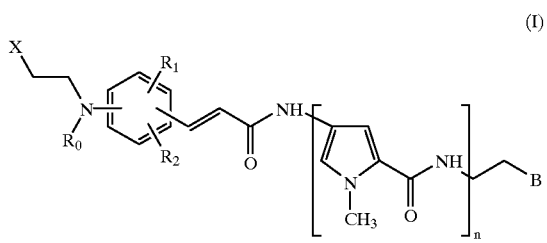

(I)

wherein:

n is 2, 3 or 4;

$R_0$ is $C_1$–$C_4$ alkyl or $C_1$–$C_3$ haloalkyl;

$R_1$ and $R_2$ are selected, each independently, from: hydrogen, $C_1$–$C_4$ alkyl optionally substituted by one or more fluorine atoms, and $C_1$–$C_4$ alkoxy;

X is a halogen atom;

B is selected from:

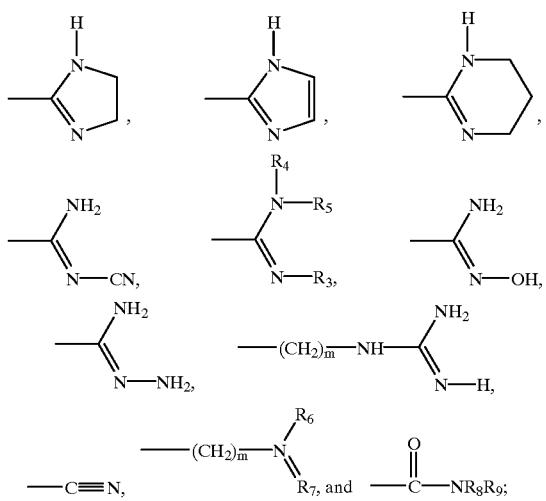

wherein $R_3$, $R_4$, $R_5$, $R_6$, $R_7$, $R_8$, and $R_9$ are, each independently, hydrogen or $C_1$–$C_4$ alkyl, and m is 0, 1 or 2; or pharmaceutically acceptable salts thereof.

The present invention includes within its scope also all the possible isomers covered by formula (I) both separately and in mixture, as well as the metabolites and the pharmaceutically acceptable bio-precursors (otherwise known as pro-drugs) of the compounds of formula (I).

The alkyl and alkoxy groups may have branched or straight chains. A $C_1$–$C_4$ alkyl group is preferably methyl or ethyl, a $C_1$–$C_4$ alkoxy group is preferably methoxy or ethoxy, while a $C_1$–$C_3$ haloalkyl group is preferably 2-chloroethyl. When substituted by one or more fluorine atoms, a $C_1$–$C_4$ alkyl group is preferably a $C_1$–$C_4$ perfluoroalkyl group, e.g. —$CF_3$.

In the phenyl ring the cinnamoyl moiety and the N(halo)alkyl-N-haloethyl-amino group are preferably in meta or para position with respect to each other.

As to the $R_1$ and $R_2$ groups, they can be in any of the free positions of the phenyl ring. In a first preferred embodiment $R_1$ is hydrogen, and $R_2$ is hydrogen, $C_1$–$C_4$ alkyl optionally substituted by one or more fluorine atoms, or $C_1$–$C_4$ alkoxy; in a second preferred embodiment both $R_1$ and $R_2$ are, each independently, $C_1$–$C_4$ alkyl optionally substituted by one or more fluorine atoms, or $C_1$–$C_4$ alkoxy. A particularly preferred value of n is 3; X is preferably chloro or bromo. Preferably, $R_3$, $R_4$, $R_5$, $R_6$, $R_7$, $R_8$, and $R_9$ are, each independently, hydrogen, methyl, or ethyl, while $R_0$ is preferably methyl, ethyl, propyl, 2-chloroethyl or 2-bromoethyl.

Pharmaceutically acceptable salts of the compounds of formula (I) are their salts with pharmaceutically acceptable, either inorganic or organic, acids. Examples of inorganic acids are hydrochloric, hydrobromic, sulfuric and nitric acid; examples of organic acids are acetic, propionic, succinic, malonic, citric, tartaric, methanesulfonic and p-toluenesulfonic acid.

A preferred class of compounds according to the present invention is that of formula (I) wherein:

n is 3;

X is chloro or bromo;

$R_0$ is ethyl, propyl, 2-chloroethyl when X is chloro, or 2-bromoethyl when X is bromo;

$R_1$ and $R_2$ are, each independently, hydrogen, —$CH_3$, —$OCH_3$, or —$CF_3$;

B is selected from:

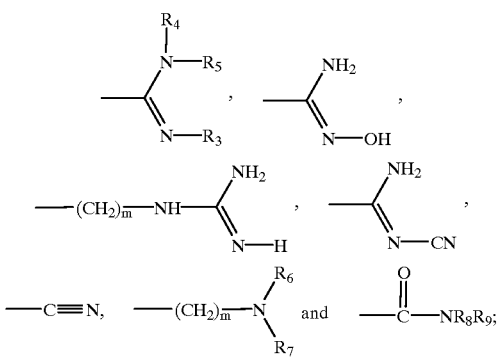

wherein $R_3$, $R_4$, $R_5$, $R_6$, $R_7$, $R_8$, and $R_9$ are, each independently, hydrogen or methyl, and m is 0 or 1; or the pharmaceutically acceptable salts thereof.

Examples of specific compounds according to the present invention, especially in the form of salts, preferably with hydrochloric acid, are the following:

1) 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine;
2) 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N-methyl-amidine;
3) 3-[1-methyl-4[1-methyl-4[1-methyl-4[4-N,N-bis(2-bromoethyl)aminocinnamoylamido]pyrrole-2-carboxamido]pyrrole-2-carboxamido]pyrrole-2-carboxamido]propionamidine;
4) 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N,N'-dimethyl-amidine;
5) 3-[1-methyl-4[1-methyl-4[1-methyl-4[4-N,N-bis(2-chloroethyl)aminocynnamoylamido]pyrrole-2-carboxamido]pyrrole-2-carboxamido]pyrrole-2-carboxamido]propionamidoxime;
6) 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propioncyanamidine;
7) 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionitrile;
8) 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamide;
9) 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]N,N-dimethylpropylamine;
10) 2-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]ethylguanidine;
11) 3-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]propionamidine;
12) 3-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]propionamidine;
13) 3-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]propionamidine;
14) 3-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]propion-N-methyl-amidine;
15) 2-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]ethylguanidine;
16) 2-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]ethylguanidine;
17) 2-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]ethylguanidine;
18) 3-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]propion-N-methyl-amidine;
19) 3-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]propion-N-methyl-amidine;
20) 3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidine;
21) 3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propion-N-methyl-amidine;
22) 3-[1-methyl-4[1-methyl-4[1-methyl-4[4-N-ethyl-N-(2-bromoethyl)aminocinnamoylamido]pyrrole-2-carboxamido]pyrrole-2-carboxamido]pyrrole-2-carboxamido]propionamidine;
23) 3-[1-methyl-4[1-methyl-4[1-methyl-4[4-N-ethyl-N-(2-chloroethyl)aminocinnamoylamido)pyrrole-2-carboxamido]pyrrole-2-carboxamido]pyrrole-2-carboxamido]propion-N,N'-dimethyl-amidine;
24) 3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidoxime;
25) 3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamide;
26) 3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]N,N-dimethylpropylamine;
27) 2-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]ethylguanidine;
28) 3-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]propionamidine;

29) 3-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]propion-N-methyl-amidine;
30) 2-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]ethylguanidine;
31) 3-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]propionamidine;
32) 3-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]propion-N-methyl-amidine;
33) 2-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]ethylguanidine;
34) 3-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]propionamidine;
35) 3-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]propion-N-methyl-amidine;
36) 2-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]ethylguanidine;
37) 3-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]propionamidine;
38) 3-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]propion-N-methyl-amidine;
39) 2-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]ethylguanidine;
40) 3-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]propionamidine;
41) 3-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]propion-N-methyl-amidine;
42) 2-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]ethylguanidine;
43) 3-[1-methyl-4[1-methyl-4[1-methyl-4[3-N,N-bis(2-chloroethyl)aminocinnamoylamido]pyrrole-2-carboxamido]pyrrole-2-carboxamido]pyrrole-2-carboxamido]propionamidine;
44) 3-[1-methyl-4[1-methyl-4[1-methyl-4[3-N,N-bis(2-chloroethyl)aminocinnamoylamido]pyrrole-2-carboxamido]pyrrole-2-carboxamido]pyrrole-2-carboxamido]propion-N-methyl-amidine;
45) 3-[1-methyl-4[1-methyl-4[1-methyl-4[3-N,N-bis(2-bromoethyl)aminocinnamoylamido]pyrrole-2-carboxamido]pyrrole-2-carboxamido]pyrrole-2-carboxamido]propionamidine; and
46) 3-[1-methyl-4[1-methyl-4[1-methyl-4[3-N-ethyl-N-(2-chloroethyl)aminocinnamoylamido]pyrrole-2-carboxamido]pyrrole-2-carboxamido]pyrrole-2-carboxamido]propionamidine.

The compounds of formula (I), and the salts thereof, can be prepared according to one of the following processes (a) and (b), which comprise:

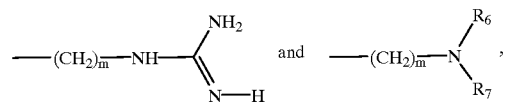

(a) when B is different from reacting a compound of formula:

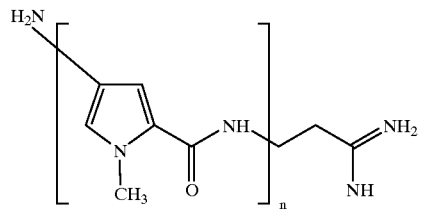

(II)

wherein n is 2, 3 or 4, with a compound of formula:

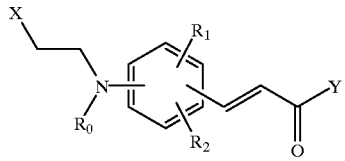

(III)

wherein:

$R_0$ is $C_1$–$C_4$ alkyl or $C_1$–$C_3$ haloalkyl;

$R_1$ and $R_2$ are selected, each independently, from: hydrogen, $C_1$–$C_4$ alkyl optionally substituted by one or more fluorine atoms, and $C_1$–$C_4$ alkoxy;

X is a halogen atom; and

Y is hydroxy or a leaving group;

so obtaining a compound of formula:

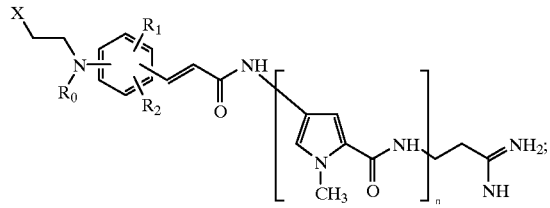

(IV)

and then, when B is different from

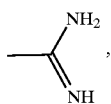, reacting compound (IV) with:

(i) $H_2N-(CH_2)_p-NH_2$, where p is 2 or 3, so obtaining a compound of formula (I) having B equal to:

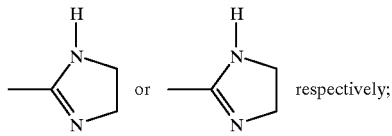 respectively;

(ii) $H_2N-CH_2-CHO$, so obtaining a compound of formula (I) having B equal to:

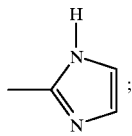;

(iii) $H_2N-CN$, so obtaining a compound of formula (I) having B equal to:

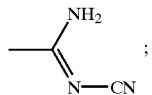;

(iv) $H_2N-OH$, so obtaining a compound of formula (I) having B equal to:

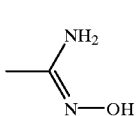

v) $H_2N-NH_2$, so obtaining a compound of formula (I) having B equal to:

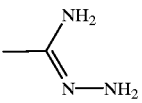

(vi) $HNR_4R_5$, so obtaining a compound of formula (I) having B equal to:

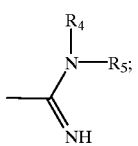

and then optionally with $H_2NR_3$, so obtaining a compound of formula (I) having B equal to:

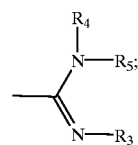

wherein $R_3$, $R_4$, and $R_5$ are, each independently, hydrogen or $C_1$–$C_4$ alkyl, with the proviso that at least one of $R_3$, $R_4$, and $R_5$ is $C_1$–$C_4$ alkyl;

(vii) succinic anhydride, so obtaining a compound of formula (I) having B equal to $-C\equiv N$;

(viii) water in an alkaline medium, so obtaining a compound of formula (I) having B equal to $-CO-NR_8R_9$ wherein $R_8$ and $R_9$ are both hydrogen;

(ix) $HNR_8R_9$, so obtaining a compound of formula (I) having B equal to:

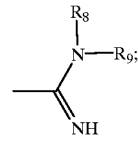

and then with water in an alkaline medium, so obtaining a compound of formula (I) having B equal to $-CO-NR_8R_9$, wherein $R_8$ and $R_9$ are, each independently, hydrogen or $C_1$–$C_4$ alkyl;

or:

(b) when B is different from

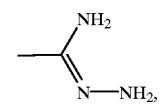

reacting a compound of formula:

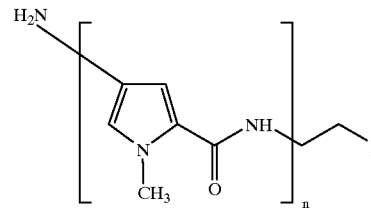

(V)

wherein n is 2, 3 or 4; B is selected from:

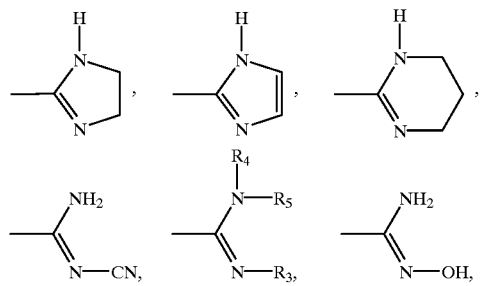

-continued

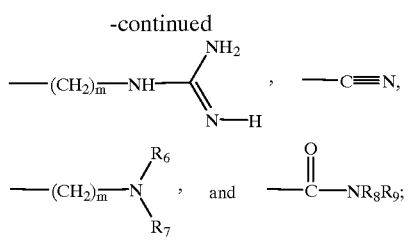

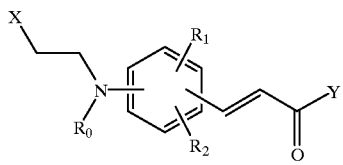

wherein $R_3$, $R_4$, $R_5$, $R_6$, $R_7$, $R_8$ and $R_9$ are, each independently, hydrogen or $C_1-C_4$ alkyl, and m is 0, 1 or with a compound of formula:

(III)

wherein:
$R_0$ is $C_1-C_4$ alkyl or $C_1-C_3$ haloalkyl;
$R_1$ and $R_2$ are selected, each independently, from: hydrogen, $C_1-C_4$ alkyl optionally substituted by one or more fluorine atoms, and $C_1-C_4$ alkoxy;
X is a halogen atom; and
Y is hydroxy or a leaving group;
so obtaining the corresponding compound of formula (I). In formula (III), Y is hydroxy or a leaving group selected, for instance, from chloro, 2,4,5-trichlorophenoxy, 2,4-dinitrophenoxy, succinimido-N-oxy, imidazolyl group, and the like.

The reaction of a compound of formula (II) (process (a)) or of formula (V) (process (b)) with a compound of formula (III) can be carried out according to known methods, for instance those described in EP-B-246,868. The reaction between a compound of formula (II) or of formula (V) and a compound of formula (III) wherein Y is hydroxy, is preferably carried out with a molar ratio (II):(III) or (V):(III) of from 1:1 to 1:2, in an organic solvent, such as, e.g., dimethylsulphoxide, hexamethylphosphotriamide, dimethylacetamide, dimethylformamide, ethanol, benzene, or pyridine, in the presence of an organic or inorganic base such as, e.g., triethylamine, diisopropyl ethylamine, or sodium or potassium carbonate or bicarbonate, and of a condensing agent such as, e.g., N-ethyl-N'-(3-dimethylamino-propyl)-carbodiimide, N,N'-dicyclohexyl-carbodiimide, or 1-hydroxy-benzotriazole hydrate. The reaction temperature may vary from about −10° C. to about 100° C., and the reaction time from about 1 to about 24 hours.

The reaction between a compound of formula (II) or of formula (V) and a compound of formula (III), wherein Y is a leaving group as defined above, may be carried out with a molar ratio (II):(III) or (V):(III) of from about 1:1 to about 1:2, in an organic solvent, such as, e.g., dimethylformamide, dioxane, pyridine, tetrahydrofurane, or mixtures thereof with water, optionally in the presence of an organic base, e.g. N,N'-diisopropylethylamine, triethylamine, or an inorganic base, e.g. sodium or potassium bicarbonate, at a temperature of from about 0° C. to about 100° C., and for a time varying from about 2 hours to about 48 hours.

The reaction between a compound of formula (IV) and one of the reactants as described at points (i), (ii), (iii), (iv), (v), (vi), or (ix) can be carried out according to known methods, for instance those reported in: U.S. Pat. No. 4,766,142, Chem. Revs. 1961, 155; J. Med. Chem. 1984, 27, 849–857; Chem. Revs. 1970, 151; and "The Chemistry of Amidines and Imidates", edited by S. Patai, John Wiley & Sons, N.Y. (1975).

The reaction of a compound of formula (IV) with succinic anhydride (see point (vii) above) is preferably carried out with a molar ratio (IV):succinic anhydride of from 1:1 to 1:3 in an organic solvent such as, e.g., dimethyl sulphoxide, dimethylformamide, in the presence of an organic or inorganic base such as, e.g., triethylamine, diisopropylethylamine, sodium or potassium carbonate, and the like. The reaction temperature may vary from about 250° C. to about 1000° C., and the reaction time from about 1 hour to about 12 hours.

The reaction with water in an alkaline medium (see points (viii) and (ix) above) may be carried out according to known methods usually employed for an alkaline hydrolysis, e.g. by treating the substrate with an excess of sodium or potassium hydroxide dissolved in water or in a mixture of water with an organic solvent, e.g. dioxane, tetrahydrofurane, or acetonitrile, at a temperature of from about 50° to about 100° C., for a time varying from about 2 hours to about 48 hours. The compounds of formula (II) are known compounds or may be prepared by known methods from known compounds: see, for instance, Arcamone et al. Gazzetta Chim. Ital. 97, 1097 (1967). The compounds of formula (III) are known compounds too or may be prepared starting from known compounds through reactions well known in organic chemistry: see, for instance, J. Med. Chem. 9, 882 (1966), J. Med. Chem. 25, 178 (1982), J. Org. Chem. 26, 4996 (1961), J. Heterocyclic Chem. 32, 1063 (1995), Synth. Commun. 24, 3129–3134 (1994).

The compounds of formula (V) are known compounds, or can be obtained by known methods (see e.g. Tetrahedron Letters 31, 1299 (1990), Anticancer Drug Design 9, 511 (1994)), such as: (i) by hydrolitic deformylation, in a basic or acid medium, of compounds of formula:

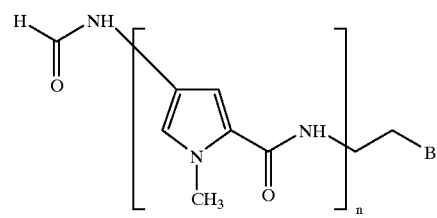

(VI)

or
(ii) by nitro-group reduction, according to known methods, of compounds of formula:

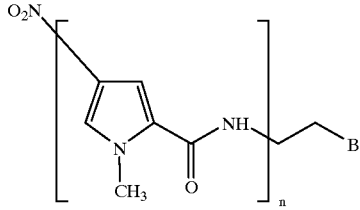

(VII)

wherein B is selected from:

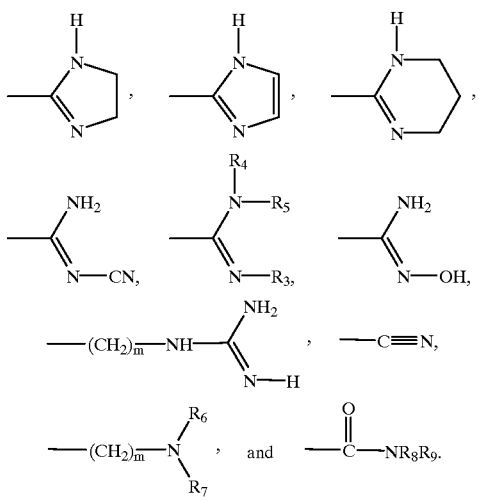

The compounds of formula (VI), except when B is equal to

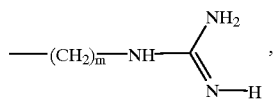

can in turn be prepared starting from distamycin analogues of formula:

(VIII)

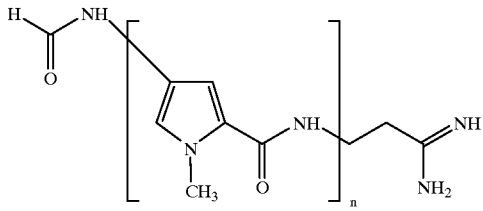

using the same reactants as reported in the second step of process a).

The compounds of formula (VII) can be obtained:
(i) from a compound of formula:

(IX)

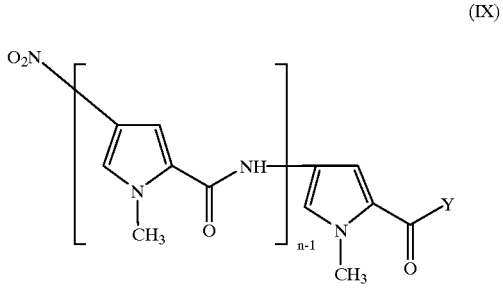

wherein n and Y are as defined above, by reaction with a compound of formula:

(X)

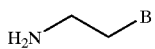

where in B is selected from:

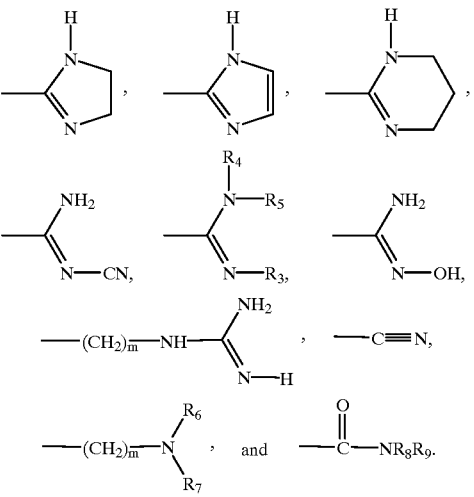

(ii) except when B is equal to

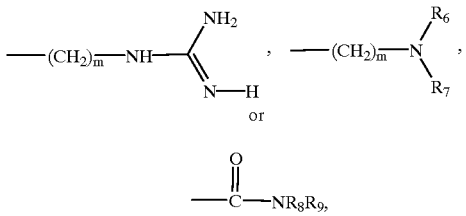

by Pinner reaction of a compound of formula:

(XI)

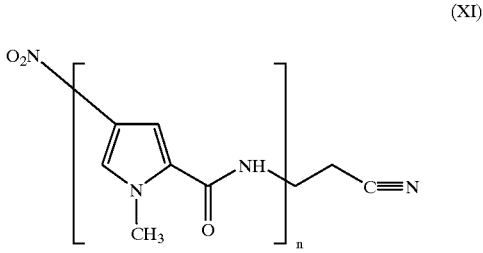

with a suitable amine compound as defined at point (i), (ii), (iii) or (vi) above.

The compounds of formulas (VIII) (IX), (X) and (XI) are known compounds, or may be obtained by known methods (see e.g. Tetrahedron, 34, 2389–2391, 1978; J. Org. Chem., 46, 3492–3497, 1981).

Salification of a compound of formula (I), as well as preparation of a free compound starting from a salt, may be carried out by known standard methods.

Well known procedures such as, e.g., fractional crystallization or chromatography, may also be followed for separating a mixture of isomers of formula (I) into the single isomers. The compounds of formula (I) may be purified by conventional techniques such as, e.g., silica gel or alumina column chromatography, and/or by recrystallization from an organic solvent such as, e.g., a lower aliphatic alcohol, e.g. methyl, ethyl or isopropyl alcohol, or dimethylformamide.

Pharmacology

The compounds of formula (I) according to the present invention are useful as antineoplastic and antiviral agents. Particularly, they show cytostatic properties towards tumor cells, so that they can be useful to inhibit growth of various tumors in mammals, including humans, such as, for instance, carcinomas, e.g. mammary carcinoma, lung carcinoma, bladder carcinoma, colon carcinoma, ovary and endometrial tumors. Other neoplasias in which the compounds of the present invention can find application are, for instance, sarcomas, e.g. soft tissue and bone sarcomas, and the hematological malignancies such as, e.g. leukemias.

The in vitro antitumor activity was evaluated by cytotoxicity studies carried out on murine $L_{1210}$ leukemia cells. Cells were derived from in vivo tumors and established in cell culture. Cells were used until the tenth passage. Cytotoxicity was determined by counting surviving cells after 48 hours treatment. The percentage of cell growth in the treated cultures was compared with that of controls. $IC_{50}$ values (concentration inhibiting 50% of the cellular growth in respect to controls) were calculated on dose-response.

The compounds of the invention were tested also in vivo on $L_{1210}$ murine leukemia and on murine reticulosarcoma M 5076, showing a very good antitumoral activity, with the following procedure. $L_{1210}$ murine leukemia was maintained in viva by i.v. serial transplantation. For experiments, $10^5$ cells were injected i.p. in CD2F1 female mice, obtained from Charles River Italy. Animals were 8 to 10 weeks old at the beginning of the experiments. Compounds were administered i.v. at day +1 after tumor cells injections. M5076 reticulosarcoma was maintained in viva by i.m. serial transplantation. For experiments, $5 \times 10^5$ cells were injected i.m. in C57B16 female mice, obtained from Charles River Italy. Animals were 8 to 10 weeks old at the beginning of the experiments. Compounds were administered i.v. at day 3, 7 and 11 after tumor injection. Survival time of mice and tumor growth were calculated and activity was expressed in term of T/C & and T.I. %.

$$T/C = \frac{\text{median survival time treated group}}{\text{median survival time untreated group}} \times 100$$

T.I.=% inhibition of tumor growth respect to control

Tox: number of mice which died for toxicity. Tox determination was made when mice died before the control and/or tested significant body weight loss and/or spleen and/or liver size reduction were observed. Following the methods described above, the representative compound 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine (internal code FCE 29381) showed in vitro an $IC_{50}$ value of 7.3 ng/ml, while in vivo, with an optimal dose (O.D.) of 6.25 mg/kg, the activity expressed as T/C %, was 267 (Tox=0/10) on $L_{1210}$ murine leukemia.

The compounds of the invention show also a remarkable effectiveness in interfering with the reproductive activity of pathogenic viruses and protect tissue cells from viral infections. For example, they show activity against DNA viruses such as, for instance, herpes, e.g. herpes simplex and herpes zoster viruses, virus vaccinia, RNA viruses such as, e.g., Rhinovirus and Adenovirus, and against retroviruses such as, for instance, sarcoma viruses, e.g., murine sarcoma virus, and leukemia viruses, e.g. Friend leukemia virus.

For example, effectiveness against herpes, coxsackie and respiratory syncytial viruses was tested in a fluid medium as follows. Serial two-fold dilutions of the compounds from 200 to 1.5 mcg/ml were distributed in duplicate 0.1 ml/well in 96 well microplates for tissue culture. Cell suspensions ($2 \times 10^5$ cells/ml) infected with about $5 \times 10^{-3}$ $TCID_{50}$ of virus/cell were immediately added 0.1 ml/well.

After 3–5 day incubation at 37° C. in $CO_2$ 5%, the cell cultures were evaluated by microscope observation and Minimum Inhibiting Concentration (MIC) was determined, MIC being the minimum concentration which determines a reduction of cytopathic effect in comparison with the infected controls.

The compounds of the invention can be administered to mammals, including humans, through the usual routes, for example, parenterally, e.g. by intravenous injection or infusion, intramuscularly, subcutaneously, topically or orally. The dosage depends on the age, weight and conditions of the patient and on the administration route. For example, a suitable dosage for administration to adult humans may range from about 0.1 to about 150–200 mg pro dose 1–4 times a day.

Further object of the present invention are pharmaceutical compositions, which comprise a compound of formula (I) as an active principle, in association with one or more pharmaceutically acceptable carrier and/or diluent.

The pharmaceutical compositions of the present invention are usually prepared following conventional methods and are administered in a pharmaceutically suitable form. For instance, solutions for intravenous injection or infusion may contain as a carrier, for example, sterile water or preferably, they may be in the form of sterile aqueous isotonic saline solutions. Suspensions or solutions for intramuscular injections may contain, together with the active compound a pharmaceutically acceptable carrier, e.g. sterile water, olive oil, ethyl oleate, glycols, e.g. propylene glycol, and if desired, a suitable amount of lidocaine hydrochloride. In the forms for topical application, e.g. creams, lotions or pastes for use in dermatological treatment, the active ingredient may be mixed with conventional oleaginous or emulsifying excipients. The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulation. Said pharmaceutical preparation may be manufactered by known techniques, for example by means of mixing, granulating, tabletting, sugar-coating or film-coating processes.

Further object of the present invention are compounds of formula (I) for use in a method for treating the human or animal body by therapy. Furthermore, the present invention provides a method for treating tumors and viral infections in a patient in need of it, which comprises administering to said patient a composition of the invention. A further object of the present invention is a combined method for treating cancer or for ameliorating the conditions of mammals, including humans, suffering from cancer, said method comprising administering a compound of formula (I), or a pharmaceutically acceptable salt thereof, and an additional antitumor agent, close enough in time and in amounts sufficient to produce a therapeutically useful effect.

The present invention also provides products containing a compound of formula (I), or a pharmaceutically acceptable salt thereof, and an additional antitumour agent as a combined preparation for simultaneous, separate or sequential use in anti-cancer therapy. The term "antitumor agent" is meant to comprise both a single antitumor drug and "cocktails" i.e. a mixture of such drugs, according to the clinical practice. Examples of antitumor agents that can be formulated with a compound of formula (I), or alternatively, can be administered in a combined method of treatment, include doxorubicin, daunomycin, epirubicin, idarubicin, etoposide, fluoro-uracil, melphalan, cyclophosphamide, 4-demethoxy daunorubicin, bleomycin, vinblastin, and mitomycin, or mixtures thereof.

The following examples are given to better illustrate the invention, but do not limit the scope of the invention itself.

EXAMPLE 1

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidine hydrochloride Step I The Intermediate ethyl N-ethyl-4-aminocinnamate To a solution of 5 g of ethyl 4-aminocinnamate in 100 ml of methanol, 0.1 ml of acetaldehyde, 1.256 g of sodium cyanoborohydride and 2.15 ml of hydrochloric acid 23% were added. The solution was stirred at room temperature for one day, then the solvent evaporated in vacuum and the crude residue purified by flash chromatography (n-exane/ethyl acetate 9/1) to yield 2.1 g of intermediate as a yellow solid.

FAB-MS: m/z 220, (60, [M+H]$^+$)

PMR (CDCl$_3$) δ:
7.61 (d, J=15.7 Hz, 1H), 7.33 (m, 2H), 6.55 (m, 2H), 6.21 (d, J=15.7 Hz, 1H), 4.22 (q, J=7.1 Hz, 2H), 3.9 (b.s., 1H), 3.19 (q, J=7.1 Hz, 2H), 1.25 (t, J=7.1 Hz, 3H), 1.28 (t, J=7.1 Hz, 3H).

By analogous procedure and using the opportune starting materials the following intermediates can be obtained:
ethyl 3-methyl-N-methyl-4-aminocinnamate;
ethyl 3,5-dimethyl-N-methyl-4-aminocinnamate;
ethyl 3-methoxy-N-methyl-4-aminocinnamate;
ethyl 3-methyl-N-ethyl-4-aminocinnamate;
ethyl 3,5-dimethyl-N-ethyl-4-aminocinnamate;
ethyl 3-methoxy-N-ethyl-4-aminocinnamate;
ethyl 3-methyl-N-propyl-4-aminocinnamate;
ethyl 3,5-dimethyl-N-propyl-4-aminocinnamate;
ethyl 3-methoxy-N-propyl-4-aminocinnamate;
ethyl N-propyl-4-aminocinnamate;
ethyl N-methyl-4-aminocinnamate; and
ethyl N-ethyl-3-aminocinnamate.

Step II

The Intermediate N-ethyl-N-(2-chloroethyl)-4-aminocinnamic acid

To a solution of 2 g of intermediate obtained from step I in 40 ml of methanol, 2.65 ml of chloroacetaldehyde (40% in water), 430 mg of sodium cyanoborohydride and 1 ml of hydrochloric acid 23% were added. The solution was stirred at room temperature for four hours then the solvent evaporated in vacuum and the crude residue purified by flash chromatography (n-exane/ethyl acetate 9/1) to yield 2 g of ethyl N-ethyl-4-aminocinnamate as a yellow oil which was dissolved in 20 ml of 37% hydrochloric acid and refluxed for two hours. The mixture was extracted with ethyl acetate (3×100 ml), the combined organic extracts were washed with water (20 ml), dried on sodium sulphate and concentrated in vacuum to yield 1.8 g of the intermediate as a yellow solid.

FAB-MS: m/z 282, (50, [M+H]$^+$)

PMR (CDCl$_3$) δ:
7.70 (d, J=15.8 Hz, 1H), 7.42 (m, 2H), 6.65 (m, 2H), 6.22 (d, J=15.8 Hz, 1H), 3.61 (m, 4H), 3.45 (q, J=7.1 Hz, 2H), 1.19 (t, J=7.1 Hz, 2H).

By analogous procedure and using the opportune starting materials the following products can be obtained:
3-methyl-N-methyl-N-(2-chloroethyl)-4-aminocinnamic acid;
3,5-dimethyl-N-methyl-N-(2-chloroethyl)-4-aminocinnamic acid;
3-methoxy-N-methyl-N-(2-chloroethyl)-4-aminocinnamic acid;
3-methyl-N-ethyl-N-(2-chloroethyl)-4-aminocinnamic acid;
3,5-dimethyl-N-ethyl-N-(2-chloroethyl)-4-aminocinnamic acid;
3-methoxy-N-ethyl-N-(2-chloroethyl)-4-aminocinnamic acid;
3-methyl-N-propyl-N-(2-chloroethyl)-4-aminocinnamic acid;
3,5-dimethyl-N-propyl-N-(2-chloroethyl)-4-aminocinnamic acid;
3-methoxy-N-propyl-N-(2-chloroethyl)-4-aminocinnamic acid;
N-propyl-N-(2-chloroethyl)-4-aminocinnamic acid;
N-methyl-N-(2-chloroethyl)-4-aminocinnamic acid; and
N-ethyl-N-(2-chloroethyl)-3-aminocinnamic acid.

Step III

The Title Compound

A solution of 200 mg of intermediate obtained from step II, 162 mg of dicyclohexylcarbodiimide and 106 mg of 1-hydroxybenzotriazole hydrate in 10 ml of DMF was stirred at 70° C. for four hours, cooled to room temperature and then added with 310 mg of 3-[1-methyl-4-[1-methyl-4-[1-methyl-4-aminopyrrole-2-carboxamido]pyrrole-2-carboxamido]pyrrole-2-carboxamido]propionamidine dihydrochloride (prepared as reported in J.Med.Chem 32, 774–778, 1989) and 118 mg of potassium bicarbonate. The mixture was stirred at room temperature for 3 hours, the solvent was evaporated in vacuum and the crude residue purified by flash chromatography (methylene chloride/methanol: 8/2) to yield 180 mg of the title compound as a yellow solid.

FAB-MS: m/z 689, (20, [M+H]$^+$)

U.V. (EtOH 95%) $\lambda_{max}$=366, $\epsilon$=41867

PMR (DMSO-d$_6$) δ:
10.00 (s, 1H), 9.94 (s, 1H), 9.91 (s, 1H), 8.95 (b.s., 2H), 8.55 (b.s., 2H), 8.21 (t, J=5.8 Hz, 1H), 7.41 (m, 2H), 7.37 (d, J=15.6 Hz, 1H), 7.27 (d, J=1.7 Hz, 1H), 7.23 (d, J=1.7 Hz, 1H), 7.17 (d, J=1.7 Hz, 1H) 7.05 (d, J=1.7 Hz, 1H), 6.95 (d, J=1.7 Hz, 1H), 6.93 (d, J=1.7 Hz, 1H),6.73 (m, 2H), 6.50 (d, J=15.6 Hz, 1H), 3.85 (s, 3H), 3.84 (s, 3H), 3.80 (s, 3H), 3.80–3.30 (m, 8H), 2.60 (m, 2H), 1.10 (t, J=7.0 Hz, 3H).

By analogous procedure and using the opportune starting materials the following products can be obtained:

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine hydrochloride FAB-MS: m/z 723, (100, [M+H]$^+$)

PMR (DMSO-d$_6$) δ:
10.01 (s, 1H), 9.97 (s, 1H), 9.94 (s, 1H), 8.95 (b.s., 2H), 8.57 (b.s., 2H), 8.24 (t, J=5.6 Hz, 1H), 7.44 (m, 2H), 7.39 (d, J=15.6 Hz, 1H), 7.29 (d, J=1.7 Hz, 1H), 7.24 (d, J=1.7 Hz, 1H), 7.18(d, J=1.7 Hz, 1H) 7.06 (d, J=1.7 Hz, 1H), 6.95 (d, J=1.7 Hz, 1H), 6.94 (d, J=1.7 Hz, 1H),6.80 (m, 2H), 6.55 (d, J=15.6 Hz, 1H), 3.90–3.60 (m, 8H), 3.86 (s, 3H), 3.85 (s, 3H), 3.81 (s, 3H), 3.50 (m, 2H), 2.60 (m, 2H).

3-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamide;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamide;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidine hydrochloride; and 3-[1-methyl-4[1-methyl-4[1-methyl-4[3-N-ethyl-N-(2-chloroethyl)aminocinnamoylamido]pyrrole-2-carboxamido]pyrrole-2-carboxamido]pyrrole-2-carboxamido]propionamidine hydrochloride.

EXAMPLE 2

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N-methyl-amidine hydrochloride Step I The Intermediate 3-[1-methyl-4[1-methyl-4[1-methyl-4-aminopyrrole-2-carboxamido]pyrrole-2-carboxamido]pyrrole-2-carboxamido]propyl-N-methyl-amidine dihydrochloride A solution of 2 g of distamycin A in 50 ml DMF was treated with 0.38 ml of methylamine hydrochloride 80%. After 8 hours additional 0.25 equivalent of methylamine hydrochloride 80% was added. The solution was evaporated to dryness and the crude residue was purified by flash chromatography (methylene chloride/methanol: 8/2) to give 1.5 g of 3[1-methyl-4[1-methyl-4[1-methyl-4-formamidopyrrole-2-carboxamido]pyrrole-2-carboxamido]pyrrole-2-carboxamido]propyl-N-methyl-amidine hydrochloride which was dissolved in 40 ml of methanol and added of 5 ml of 2 N hydrochloric acid. The reaction was stirred at room temperature for two days, the solvent evaporated in vacuum and the solid residue suspended in 200 ml of ethyl acetate, yielding after filtration 1.4 g of the intermediate.

FAB-MS: m/z 468, (40, [M+H]$^+$)

PMR (DMSO-d$_6$) δ:
10.20 (s, 3H), 10.18 (s, 1H), 9.98 (s, 1H), 9.65 (m, 1H), 9.20 (s, 1H), 8.63(s, 1H), 8.25 (t, J=5.8 Hz, 1H), 7.25 (d, J=1.7 Hz, 1H), 7.19 (d, J=1.7 Hz, 1H), 7.11 (d, J=1.7 Hz, 1H) 7.08 (d, J=1.7 Hz, 1H), 7.05 (d, J=1.7 Hz, 1H), 6.91 (d, J=1.7 Hz, 1H), 3.90 (s, 3H), 3.85 (s, 3H), 3.79 (s, 3H), 3.60–3.40 (m, 2H), 2.80 (d, J=6 Hz, 3H), 2.61 (m, 2H).

Step II

The Title Compound

A solution of 213 mg of 4-N,N-bis(2-chloroethyl)aminocinnamic acid, 152 mg of dicyclohexylcarbodiimide and 100 mg of 1-hydroxybenzotriazole hydrate in 15 ml of DMF was stirred at 70° C. for four hours, cooled to room temperature and then added of 200 mg of intermediate obtained from step I and 148 mg of potassium bicarbonate. The mixture was stirred at room temperature for 3 hours, the solvent was evaporated in vacuum and the crude residue purified by flash chromatography (methylene chloride/methanol: 8/2) to yield 100 mg of the title compound as a yellow solid.

FAB-MS: m/z 737, (20, [M+H]$^+$)

PMR (DMSO-d$_6$) δ:
10.05 (s, 1H), 9.96 (s, 1H), 9.93 (s, 1H), 9.30–8.40 (b.s., 3H), 8.22 (t, J=5.8 Hz, 1H), 7.45 (m, 2H); 7.41 (d, J=15.7 Hz, 1H), 7.28 (d, J=1.8 Hz, 1H), 7.25 (d, J=1.8 Hz, 1H), 7.18 (d, J=1.8 Hz, 1H) 7.08 (d, J=1.8 Hz, 1H), 6.95 (d, J=1.8 Hz, 1H), 6.93 (d, J=1.8 Hz, 1H), 6.80 (m, 2H), 6.55 (d, J=15.7 Hz, 1H), 3.90–3.70 (m, 8H), 3.85 (s, 3H), 3.80 (s, 3H), 3.76 (s, 3H), 3.50 (m, 2H), 2.78 (s, 3H), 2.61 (t, J=6.7 Hz, 2H).

By analogous procedure and using the opportune starting materials the following products can be obtained:

3-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1]-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]propion-N-methyl-amidine hydrochloride; and 3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]-N,N-dimethylpropylamine hydrochloride.

EXAMPLE 3

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N,N'-dimethyl-amidine hydrochloride Step I The Intermediate 3-[1-methyl-4[1-methyl-4[1-methyl-4-aminopyrrole-2-carboxamido]pyrrole-2-carboxamido]pyrrole-2-carboxamido]propyl-N,N'-dimethyl-amidine dihydrochloride A solution of 1.5 g of distamycin A in 40 ml DMF was heated at 80° C. and treated with 4 ml of methylamine hydrochloride 80%. After 4 hours additional 5 equivalent (4 ml) of methylamine hydrochloride 80% was added. The solution was evaporated to dryness and the crude residue was purified by flash chromatography (methylene chloride/methanol: 8/2) to give 1.2 g of, 3-[1-methyl-4[1-methyl-4[1-methyl-4-formamadopyrrole-2-carboxamido]pyrrole-2-carboxamido]pyrrole-2-carboxamido]propyl-N,N'-dimethyl-amidine hydrochloride which was dissolved in 40 ml of methanol and added of 5 ml of 2 N hydrochloric acid solution. The reaction was stirred at room temperature for two days, the solvent evaporated in vacuum and the solid residue suspended in 200 ml of ethyl acetate, yielding after filtration 1.4 g of the intermediate.

FAB-MS: m/z 482, (45, [M+H]$^+$)

PMR (DMSO-d$_6$) δ:
10.21 (s, 3H), 10.18 (s, 1H), 9.98 (s, 1H), 9.61 (m, 1H), 8.85 (s, 1H), 8.39 (t, J=5.8 Hz, 1H), 8.00–7.70 (b.s., 1H), 7.28 (d, J=1.7 Hz, 1H), 7.22 (d, J=1.7 Hz, 1H), 7. 12 (d, J=1.7 Hz, 1H) 7.08 (d, J=1.7 Hz, 1H), 7.03 (d, J=1.7 Hz, 1H), 6.92 (d, J=1.7 Hz, 1H), 3.92 (s, 3H), 3.89 (s, 3H), 3.86 (s, 3H), 3.60–3.40 (m, 2H), 3.02 (d, J=6 Hz, 3H), 2.80 (d, J=6 Hz, 3H), 2.72 (m, 2H).

Step II

The Title Compound

A solution of 140 mg of 4-N,N-bis(2-chloroethyl)aminocinnamic acid, 100 mg of dicyclohexylcarbodiimide and 65 mg of 1-hydroxybenzotriazole hydrate in 15 ml of DMF was stirred at 80° C. for four hours, cooled at room temperature and then added with 180 mg of intermediate obtained from step I and 128 mg of potassium bicarbonate. The mixture was stirred at room temperature for 3 hours, the solvent was evaporated in vacuum and the crude residue purified by flash chromatography (methylene chloride/methanol: 8/2) to yield 100 mg of the title compound as a yellow solid.

FAB-MS: m/z 751, (25, [M+H]$^+$)

PMR (DMSO-d$_6$) δ:
10.03 (s, 1H), 9.95 (s, 1H), 9.93 (s, 1H), 9.40 (b.s., 1H), 8.55 (b.s., 1H), 8.29 (t, J=5.8 Hz, 1H), 7.44 (m, 2H), 7.39 (d, J=15.7 Hz, 1H), 7.28 (d, J=1.8 Hz, 1H), 7.23 (d, J=1.8 Hz, 1H), 7.19 (d, J=1.8 Hz, 1H) 7.06 (d, J=1.8 Hz, 1H), 6.94 (d, J=1.8 Hz, 1H), 6.93 (d, J=1.8 Hz, 1H),6.80 (m, 2H), 6.54 (d, J=15.7 Hz, 1H), 3.90–3.60 (m, 8H), 3.85 (s, 3H), 3.84 (s, 3H), 3.80 (s, 3H), 3.45 (m, 2H), 3.01 (s, 3H), 2.78 (s, 3H), 2.72 (t, J=6.7 Hz, 2H).

By analogous procedure and using the opportune starting material the following product can be obtained:

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propion-N,N'-dimethyl-amidine hydrochloride.

EXAMPLE 4

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propioncyanamidine Step I The Intermediate 3-[1-methyl-4[1-methyl-4[1-methyl-4-aminopyrrole-2-carboxamido]pyrrole-2-carboxamido]pyrrole-2-carboxamido] propioncyanamidine hydrochloride To a solution of 324 mg of cyanamide in 20 ml of DMF were added 186 mg of sodium hydride. The mixture was stirred at room temperature for 30 min. and then added to a solution of 1 g of distamycin A in 10 ml DMF. The solution was stirred at room temperature for two hours, then acetic acid was added until pH=7. The solvent was removed at reduced pressure and the crude residue purified by flash chromatography (methylene chloride/methanol: 9/1) to give 900 mg of 3-[1-methyl-4[1-methyl-4[1-methyl-4-formamidopyrrole-2-carboxamido]pyrrole-2-carboxamido]pyrrole-2-carboxamido]propioncyanamidine which was dissolved with 50 ml of methanol and added of 5 ml of 2 N hydrochloric acid. The reaction was stirred at room temperature for two days, solvent evaporated in vacuum and the solid residue suspended in 200 ml of ethyl acetate, yielding after filtration 600 mg of the intermediate.

FAB-MS: m/z 479, (65, [M+H]$^+$)

PMR (DMSO-d$_6$) δ:
10.11 (s, 3H), 9.97 (s, 1H), 9.80–9.60 (b.s., 2H), 8.50–8.00 (b.s., 3H), 7.40 (t, J=5.8 Hz, 1H), 7.25 (d, J=1.7 Hz, 1H), 7.19 (d, J=1.7 Hz, 1H), 7.08 (d, J=1.7 Hz, 1H), 7.06 (d, J=1.7 Hz, 1H), 6.94 (d, J=1.7 Hz, 1H), 6.88 (d, J=1.7 Hz, 1H), 3.81 (s, 3H), 3.79 (s, 3H), 3.75 (s, 3H), 3.41 (m, 2H), 2.70 (m, 2H).

Step II

The Title Compound

A solution of 95 mg of 4-N,N-bis(2-chloroethyl) aminocinnamic acid, 65 mg of dicyclohexylcarbodiimide and 45 mg of 1-hydroxybenzotriazole hydrate in 15 ml of DMF was stirred at 80° C. for four hours, cooled to room temperature and then added with 110 mg of intermediate obtained from step I and 40 mg of potassium bicarbonate. The mixture was stirred at room temperature for 3 hours, the solvent was evaporated in vacuum and the crude residue purified by flash chromatography (methylene chloride/methanol: 8/2) to yield 90 mg of the title compound as a yellow solid.

FAB-MS: m/z 748, (15, [M+H]$^+$); 272, (100)

PMR (DMSO-d$_6$ 45° C.) δ:
9.87 (s, 1H), 9.83 (s, 1H), 9.80 (s, 1H), 8.60–7.90 (b.s., 3H), 7.44 (m, 2H), 7.40 (d, J=15.8 Hz, 1H), 7.25 (d, J=1.7 Hz, 1H), 7.22 (d, J=1.7 Hz, 1H), 7.17 (d, J=1.7 Hz, 1H) 7.03 (d, J=1.7 Hz, 1H), 6.92 (d, J=1.7 Hz, 1H), 6.87 (d, J=1.7 Hz, 1H), 6.81 (m, 2H), 6.53 (d, J=15.8 Hz, 1H), 3.90–3.70 (m, 8H), 3.86 (s, 3H), 3.85 (s, 3H), 3.81 (s, 3H), 3.45 (b.s. 2H), 2.60 (b.s., 2H).

EXAMPLE 5

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidoxime A solution of 180 mg of 3-[1-methyl-4[1-methyl-4[1-methyl-4[4-N,N-bis(2-chloroethyl)aminocinnamoylamido] pyrrole-2-carboxamido]pyrrole-2-carboxamido]pyrrole-2-carboxamido]propionamidine hydrochloride (prepared as reported in Example 1) in 20 ml DMF was heated to 80° C. and treated with 0.48 ml of hydroxylamine 1M in DMF. After 30 min. additional 1 equivalent of hydroxylamine 1M in DMF was added. The solution was evaporated to dryness and the crude residue was purified by flash chromatography (methylene chloride/methanol: 9/1) to give 90 mg of the title compound as a white solid.

FAB-MS: m/z 739, (20, [M+H]$^+$); 272, (100)

PMR (DMSO-d$_6$) δ:
12.30 (b.s., 1H), 10.02 (s, 1H), 9.96 (s, 1H), 9.91 (s, 1H), 9.7 (b.s., 2H), 8.05 (t, J=5.6 Hz, 1H), 7.45 (m, 2H), 7.39 (d, J=15.6 Hz, 1H), 7.29 (d, J=1.7 Hz, 1H), 7.24 (d, J=1.7 Hz, 1H), 7.18 (d, J=1.7 Hz, 1H), 7.05 (d, J=1.7 Hz, 1H), 6.93 (d, J=1.7 Hz, 1H), 6.89 (d, J=1.7 Hz, 1H), 6.80 (m, 2H), 6.53 (d, J=15.6 Hz, 1H), 3.90–3.70 (m, 8H), 3.87 (s, 3H), 3.84 (s, 3H), 3.81 (s, 3H), 3.40 (m, 2H), 2.36 (m, 2H).

By analogous procedure and using the opportune starting materials the following product can be obtained:
3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidoxime.

EXAMPLE 6

2-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]ethylguanidine hydrochloride Step I The Intermediate 2-aminoethylguanidine dihydrochloride A solution of commercial N-BOC-ethylendiamine (1 g) in dry ethanol (100 ml) and 2-methyl-2-thiopseudourea hydroiodide (1.5 g) was refluxed for 8 hours. The solvent was removed at reduced pressure and the crude residue purified by flash chromatography (methylene chloride/methanol: 9/1) to yield 1.5 g of N-BOC-2-aminoethylguanidine hydroiodide as a yellow oil which was dissolved in methanolic hydrochloric acid solution 5N (20 ml) and stirred at room temperature for 3 hours. The white precipitate was collected, washed with dry ethanol, affording 700 mg of the intermediate.

FAB-MS: m/z 103, (20, [M+H]$^+$)

PMR (DMSO-d$_6$) δ:
8.38 (b.s., 3H), 7.97 (t, J=6 Hz, 1H), 7.51 (b.s., 4H), 3.45 (m, 2H), 2.92 (m, 2H).

Step II

The Intermediate 2-[1-methyl-4[1-methyl-4[1-methyl-4-aminopyrrole-2-carboxamido]pyrrole-2-carboxamido]pyrrole-2-carboxamido]ethylguanidine dihydrochloride A solution of 1-methyl-4[1-methyl-4[1-methyl-4-nitropyrrole-2-carboxamido]pyrrole-2-carboxamido] pyrrole-2-carboxylic acid (590 mg) (prepared as reported in Tetrahedron 34,2389–2391,1978) in 20 ml of DMF, 2-aminoethylguanidine dihydrochloride (500 mg), 1-hydroxybenzotriazole hydrate(350 mg), dicycloexylcarbodiimide (880 mg), and sodium bicarbonate (385 mg) was stirred at 70° C. for 4 hours. The solution obtained after filtration was evaporated in vacuum and the residue purified by flash chromatography (methylene chloride/methanol: 8/2) to yield 800 mg of 2-[1-methyl-4[1-methyl-4[1-methyl-4-nitropyrrole-2-carboxamido]pyrrole-2-carboxamido] pyrrole-2-carboxamido]ethylguanidine hydrochloride, which was dissolved in methanol (100 ml), added with 1N hydrochloric acid solution (2 ml) and reduced over Pd catalyst (10% on charcoal) in hydrogen atmosphere (50 psi) in a Parr apparatus. The solution obtained after filtration of the catalyst was evaporated in vacuum and the solid residue washed with dry ethanol to yield 750 mg of the intermediate as a brown powder.

FAB-MS: m/z 469, (15, [M+H]$^+$)

PMR (DMSO-d$_6$) δ:
10.38–10.11 (b.s., 4H), 9.98 (s, 1H), 8.28 (b.s., 1H), 8.19 (d, J=1.7 Hz, 1H), 7.73, (b.s., 1H), 7.63 (d, J=1.7 Hz, 1H), 7.60–7.00 (b.s., 4H), 7.28 (d, J=1.7 Hz, 1H), 7.20 (d, J=1.7 Hz, 1H), 7.1 (d, J=1.7 Hz, 1H), 6.92 (d, J=1.7 Hz, 1H), 3.93 (s, 3H), 3.90 (s, 3H), 3.82 (s, 3H), 3.28 (m, 4H).

By analogous procedure and using the opportune starting materials the following products can be obtained:
3-[1-methyl-4[1-methyl-4[1-methyl-4-aminopyrrole-2-carboxamido]pyrrole-2-carboxamido]pyrrole-2-carboxamido]propioncyanamidine hydrochloride;
3-[1-methyl-4[1-methyl-4[1-methyl-4-aminopyrrole-2-carboxamido]pyrrole-2-carboxamido]pyrrole-2-carboxamido]propion-N-methyl-amidine dihydrochloride;
3-[1-methyl-4[1-methyl-4[1-methyl-4-aminopyrrole-2-carboxamido]pyrrole-2-carboxamido]pyrrole-2-carboxamido]propion-N,N'-dimethyl-amidine dihydrochloride;
3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionitrile; and 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]N,N-dimethylpropylamine dihydrochloride.

Step III

The Title Compound

A solution of 95 mg of 4-N,N-bis(2-chloroethyl) aminocinnamic acid, 65 mg of dicyclohexylcarbodiimide and 45 mg of 1-hydroxybenzotriazole hydrate in 15 ml of DMF was stirred at 80° C. for four hours, cooled to room temperature and then added with 168 mg of intermediate obtained from step II and 40 mg of potassium bicarbonate. The mixture was stirred at room temperature for 3 hours, the solvent was evaporated in vacuum and the crude residue purified by flash chromatography (methylene chloride/methanol: 8/2) to yield 100 mg of the title compound as a yellow solid.

FAB-MS: m/z 738, (20, [M+H]$^+$)

PMR (DMSO-d$_6$) δ:
10.04 (s, 1H), 9.96 (s, 1H), 9.94 (s, 1H), 8.14 (t, J=5.7 Hz, 1H), 7.76 (b.s., 1H), 7.42 (m, 2H), 7.40–7.10 (b.s., 4H), 7.39 (d, J=15.7 Hz, 1H), 7.28 (d, J=1.7 Hz, 1H), 7.24 (d, J=1.7 Hz, 1H), 7.19 (d, J=1.7 Hz, 1H), 7.06 (d, J=1.7 Hz, 1H), 6.91 (d, J=1.7 Hz, 1H), 6.87 (d, J=1.7 Hz, 1H), 6.80 (m, 2H), 6.55 (d, J=15.7 Hz, 1H), 3.85 (s, 3H), 3.84 (s, 3H), 3.81 (s, 3H), 3.80–3.60 (m, 8H), 3.40 (m, 2H), 3.30 (m, 2H).

By analogous procedure and using the opportune starting materials the following products can be obtained:

3-[1-methyl-4[1-methyl-4[1-methyl-4[3-N,N-bis(2-chloroethyl)aminocinnamoylamido]pyrrole-2-carboxamido]pyrrole-2-carboxamido]pyrrole-2-carboxamido]propionamidine hydrochloride
FAB-MS: m/z 723, (100, [M+H]$^+$)
PMR (DMSO-d$_6$) δ:
10.20 (s, 1H), 9.96 (s, 1H), 9.91 (s, 1H), 8.9 (b.s., 2H), 8.6 (b.s., 2H), 8.21 (t, J=5.8 Hz, 1H), 6.7–7.3 (m, 10H), 7.47 (d, J=15.4 Hz, 1H), 6.74 (d, J=15.4 Hz, 1H), 3.85 (s, 3H), 3.83 (s, 3H), 3.80 (s, 3H), 3.75 (s, 8H), 3.49 (m, 2H), 2.60 (t, J=6.5 Hz, 2H).

2-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]ethylguanidine hydrochloride;

2-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]ethylguanidine hydrochloride;

3-[1-methyl-4[1-methyl-4[1-methyl-4[4-N,N-bis(2-bromoethyl)aminocinnamoylamido]pyrrole-2-carboxamido]pyrrole-2-carboxamido]pyrrole-2-carboxamido]propionamidine hydrobromide;

3-[1-methyl-4[1-methyl-4[1-methyl-4[4-N-ethyl-N-(2-bromoethyl)aminocinnamoylamido]pyrrole-2-carboxamido]pyrrole-2-carboxamido]pyrrole-2-carboxamido]propionamidine hydrobromide;

3-[1-methyl-4[1]-methyl-4[1-methyl-4[4-N,N-bis(2-chloroethyl)aminocinnamoylamido]pyrrole-2-carboxamido]pyrrole-2-carboxamido]pyrrole-2-carboxamido]propionitrile;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]-N,N-dimethylpropylamine hydrochloride;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]N,N-dimethylpropylamine hydrochloride; and 3-[1-methyl-4[1-methyl-4[1-methyl-4[3-N,N-bis(2-bromoethyl)aminocinnamoylamido]pyrrole-2-carboxamido]pyrrole-2-carboxamido]pyrrole-2-carboxamido]propionamidine hydrobromide.

EXAMPLE 7

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidoxime Step I The Intermediate 3-[1-methyl-4[1-methyl-4[1-methyl-4-aminopyrrole-2-carboxamido]pyrrole-2-carboxamido]pyrrole-2-carboxamido] propionamidoxime hydrochloride 1.2 g of 3-[1-methyl-4-[1-methyl-4-[1-methyl-4-nitropyrrole-2-carboxamido]pyrrole-2-carboxamido] pyrrole-2-carboxamido]propionitrile (prepared as reported in J.Med.Chem 22,1296–1301,1979) was suspended in dry ethanol and the solution saturated with dry hydrogen chloride. After 24 hours at room temperature, the solvent was evaporated in vacuum and the residue treated with two equivalents of solution of hydroxylamine in dry ethanol. After 24 hours at room temperature, the solvent was evaporated in vacuum and the residue purified by flash chromatography yielding 500 mg of 3-[1-methyl-4[1-methyl-4[1-methyl-4-nitropyrrole-2-carboxamido]pyrrole-2-carboxamido]pyrrole-2-carboxamido]propionamidoxime which was dissolved in a mixture of methanol-dioxane-10% hydrochloric acid (4:1:1) and reduced over Pd catalyst (10% on charcoal) in hydrogen atmosphere (50 psi) in a Parr apparatus. The solution obtained after filtration of the catalyst was evaporated in vacuum, and the solid residue suspended in dry ethanol, and filtered to yield 500 mg of intermediate.

FAB-MS: m/z 480

PMR (DMSO-$d_6$) δ:
10.18 (b.s., 6H), 9.98 (s, 1H), 8.32 (t, J=5.7 Hz, 1H), 7.25 (d, J=1.7 Hz, 1H), 7.20 (d, J=1.7 Hz, 1H), 7.16 (d, J=1.7 Hz, 1H), 7.12 (d, J=1.7 Hz, 1H), 7.10 (d, J=1.7 Hz, 1H), 6.93 (d, J=1.7 Hz, 1H), 3.89 (s, 3H), 3.86 (s, 3H), 3.82 (b.s., 7H), 3.50 (m, 2H), 2.72 (m, 2H).

By analogous procedure and using the opportune starting materials the following product can be obtained:

3-[1-methyl-4[1-methyl-4[1-methyl-4-aminopyrrole-2-carboxamido]pyrrole-2-carboxamido]pyrrole-2-carboxamido]propioncyanamidine hydrochloride;

3-[1-methyl-4[1-methyl-4[1-methyl-4-aminopyrrole-2-carboxamido]pyrrole-2-carboxamido]pyrrole-2-carboxamido]propion-N-methyl-amidine dihydrochloride; and 3-[1-methyl-4[1-methyl-4[1-methyl-4-aminopyrrole-2-carboxamido]pyrrole-2-carboxamido]pyrrole-2-carboxamido]propion-N,N'-dimethyl-amidine dihydrochloride.

Step II

The Title Compound

A solution of 200 mg of 4-N,N-bis(2-chloroethyl)aminocinnamic acid, 162 mg of dicyclohexylcarbodiimide and 106 mg of 1-hydroxybenzotriazole hydrate in 10 ml of DMF was stirred at 70° C. for four hours, cooled to room temperature and then added with 310 mg of intermediate obtained from step I and 118 mg of potassium bicarbonate. The mixture was stirred at room temperature for 3 hours, the solvent was evaporated in vacuum and the crude residue purified by flash chromatography (methylene chloride/methanol: 8/2) to yield 180 mg of the title compound as a yellow solid.

FAB-MS: m/z 739, (20, [M+H]$^+$); 272, (100)

PMR (DMSO-$d_6$) δ:
12.30 (b.s., 1H), 10.02 (s, 1H), 9.96 (s, 1H), 9.91 (s, 1H), 9.7 (b.s., 2H), 8.05 (t, J=5.6 Hz, 1H), 7.45 (m, 2H), 7.39 (d, J=15.6 Hz, 1H), 7.29 (d, J=1.7 Hz, 1H), 7.24 (d, J=1.7 Hz, 1H), 7.18 (d, J=1.7 Hz, 1H), 7.05 (d, J=1.7 Hz, 1H), 6.93 (d, J=1.7 Hz, 1H), 6.89 (d, J=1.7 Hz, 1H), 6.80 (m, 2H), 6.53 (d, J=15.6 Hz, 1H), 3.90–3.70 (m, 8H), 3.87 (s, 3H), 3.84 (s, 3H), 3.81 (s, 3H), 3.40 (m, 2H), 2.36 (m, 2H).

By analogous procedure and using the opportune starting materials the following products can be obtained:

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N,N'-dimethyl-amidine hydrochloride;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propioncyanamidine;

3-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propion-N,N'-dimethyl-amidine hydrochloride;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidoxime;

3-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]propion-N-methyl-amidine hydrochloride;

3-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]propionamidine hydrochloride;

3-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]propionamidine hydrochloride; and 3-[1-methyl-4[1-methyl-4[1-methyl-4[3-N,N-bis(2-chloroethyl)aminocinnamoylamido]pyrrole-2-carboxamido]pyrrole-2-carboxamido]pyrrole-2-carboxamido]propion-N-methyl-amidine hydrochloride.

EXAMPLE 8

Tablets each weighing 0.250 g and containing 50 mg of the active substance can be manufactured as follows:

| Composition for 10,000 mg tablets | |
|---|---|
| 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine hydrochloride | 500 g |
| Lactose | 1,400 g |
| Corn starch | 500 g |
| Talc powder | 80 g |
| Magnesium stearate | 20 g |

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine hydrochloride, lactose and half of the corn starch were mixed; the mixture was then forced through a sieve of 0.5 mm mesh size.

Corn starch (10 g) was suspended in warm water (90 ml) and the resulting paste was used to granulate the powder. The granulate was dried, comminuted on a sieve of 1.4 mm mesh size, then the remaining quantity of starch, talc and magnesium stearate was added, carefully mixed and processed into tablets.

EXAMPLE 9

Capsules, each dosed at 0.200 g and containing 20 mg of the active substance can be prepared as follows:

| Composition for 500 mg capsules | |
|---|---|
| 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine hydrochloride | 10 g |
| Lactose | 80 g |
| Corn starch | 5 g |
| Magnesium stearate | 5 g |

This formulation can be encapsulated in two-piece hard gelatin capsules and dosed at 0.200 g for each capsule.

EXAMPLE 10
Intramuscular Injection 25 mg/ml

An injectable pharmaceutical composition can be manufactured by dissolving 25 g of 3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine hydrochloride in sterile propyleneglycol (1000 ml) and sealing ampoules of 1–5 ml.

What is claimed is:

1. A compound of formula (I):

(I)

wherein:

n is 2, 3 or 4;

$R_0$ is $C_1$–$C_4$ alkyl or $C_1$–$C_3$ haloalkyl;

$R_1$ and $R_2$, which may be the same or different, are each selected from hydrogen, $C_1$–$C_4$ alkyl optionally substituted by one or more fluorine atoms, and $C_1$–$C_4$ alkoxy;

X is a halogen atom;

B is selected from:

wherein $R_3$, $R_4$, $R_5$, $R_6$, $R_7$, $R_8$, and $R_9$, which may be the same or different, are each hydrogen or $C_1$–$C_4$ alkyl, and m is 0, 1 or 2; or pharmaceutically acceptable salt thereof.

2. A compound according to claim 1, wherein:

n is 3;

X is chloro or bromo;

$R_0$ is ethyl, propyl, 2-chloroethyl when X is chloro, or 2-bromoethyl when X is bromo;

$R_1$ and $R_2$, which may be the same or different, are each hydrogen, —$CH_3$, —$CH_3$, or —$CF_3$;

B is selected from:

wherein $R_3$, $R_4$, $R_5$, $R_6$, $R_7$, $R_8$, and $R_9$, which may be the same or different, are each hydrogen or methyl, and m is 0 or 1.

3. A compound according to claim 1, selected from:

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N-methyl-amidine;

3-[1-methyl-4[1-methyl-4[1-methyl-4[4-N,N-bis(2-bromoethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propion-N,N'-dimethyl-amidine;

3-[1-methyl-4[1-methyl-4[1-methyl-4[4-N,N-bis(2-chloroethyl)aminocynnamoylamido]pyrrole-2-carboxamido]pyrrole-2-carboxamido]pyrrole-2-carboxamido]propionamidoxime;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propioncyanamidine;

3-[1-methyl-4[1-methyl-4[1-methyl-4[4-N,N-bis(2-chloroethyl)aminocinnamoylamido]pyrrole-2- carboxamido]pyrrole-2-carboxamido]pyrrole-2-carboxamido]propionitrile;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamide;

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]N,N-dimethylpropylamine;

2-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]propionamidine;

3-[1-methyl-4[1-methyl 4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]propion-N-methyl-amidine;

2-[1-methyl-4[1-methyl-4[1-methyl-4[3-methyl-4-N,N-bis(2-chloroethyl)aminocinnamoylamido]pyrrole-2-carboxamido]pyrrole-2-carboxamido]pyrrole-2-carboxamido]ethylguanidine;

2-[1-methyl-4[1-methyl-4[1-methyl-4[3,5-dimethyl-4-N,N-bis(2 -chloroethyl)aminocinnamoylamido]pyrrole-2-carboxamido]pyrrole-2-carboxamido]pyrrole-2-carboxamido]ethylguanidine;

2-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[3,5-dimethyl-4-N,N-bis(2-chloroethyl)aminocinnamoylamido]pyrrole-2-carboxamido]pyrrole-2-carboxamido]pyrrole-2-carboxamido]propion-N-methyl-amidine;

3-[1-methyl-4[1-methyl-4[1-methyl-4[3-methoxy-4-N,N-bis(2-chloroethyl)aminocinnamoylamido]pyrrole-2-carboxamido]pyrrole-2-carboxamido]pyrrole-2-carboxamido]propion-N-methyl-amidine;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propion-N-methyl-amidine;

3-[1-methyl-4[1-methyl-4[1-methyl-4[4-N-ethyl-N-(2-bromoethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propion-N,N'-dimethyl-amidine;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamidoxime;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]propionamide;

3-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]N,N-dimethylpropylamine;

2-[1-methyl-4[1-methyl-4[1-methyl-4[4-N-ethyl-N-(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]propion-N-methyl-amidine;

2-[1-methyl-4[1-methyl-4[1-methyl-4[4-N-methyl-N-(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]propion-N-methyl-amidine;

2-[1-methyl-4[1-methyl-4[1-methyl-4[4-N-propyl-N-(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]propion-N-methyl-amidine;

2-[1-methyl-4[1-methyl-4[1-methyl-4[3-methyl-4-N-ethyl-N-(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]propion-N-methyl-amidine;

2-[1-methyl-4[1-methyl-4[1-methyl-4[3-methoxy-4-N-ethyl-N-(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[3,5-dimethyl-4-N-ethyl-N-(2-chloroethyl)aminocinnamoylamido]pyrrole- 2-carboxamido]pyrrole-2-carboxamido]pyrrole-2-carboxamido]propion-N-methyl-amidine;

2-[1-methyl-4[1-methyl-4[1-methyl-4[3,5-dimethyl-4-N-ethyl-N-(2-chloroethyl)aminocinnamoylamido]pyrrole-2-carboxamido]pyrrole-2-carboxamido]pyrrole-2-carboxamido]ethylguanidine;

3-[1-methyl-4[1-methyl-4[1-methyl-4[3-N,N-bis(2-chloroethyl)aminocinnamoylamido]pyrrole-2-carboxamido]pyrrole-2-carboxamido]pyrrole-2-carboxamido]propionamidine;

3-[1-methyl-4[1-methyl-4[1-methyl-4[3-N,N-bis(2-chloroethyl)aminocinnamoylamido]pyrrole-2-carboxamido]pyrrole-2 -carboxamido]pyrrole-2-carboxamido]propion-N-methyl-amidine;

3-[1-methyl-4[1-methyl-4[1-methyl-4[3-N,N-bis(2-bromoethyl)aminocinnamoylamido]pyrrole-2-carboxamido]pyrrole-2-carboxamido]pyrrole-2-carboxamido]propionamidine; and 3-[1-methyl-4[1-methyl-4[1-methyl-4[3-N-ethyl-N-(2-chloroethyl)aminocinnamoylamido]pyrrole-2-carboxamido]pyrrole-2-carboxamido]pyrrole-2-carboxamido]propionamidine;

and the pharmaceutically acceptable salts thereof.

4. A process for preparing a compound as claimed in claim 1, which process comprises:

(a) when B is different from

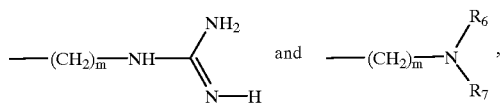

reacting a compound of formula:

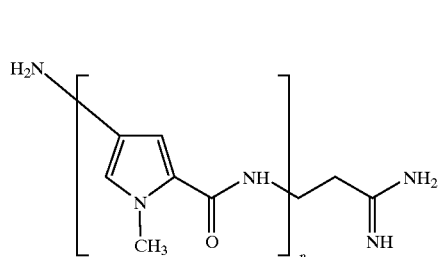

wherein n is 2, 3 or 4, with a compound of formula:

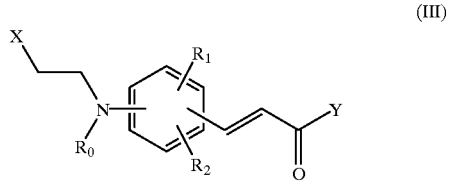

wherein:
R₀ is $C_1$–$C_4$ alkyl or $C_1$–$C_3$ haloalkyl;
R₁ and R₂, which may be the same or different, are each selected from: hydrogen, $C_1$–$C_4$ alkyl optionally substituted by one or more fluorine atoms, and $C_1$–$C_4$ alkoxy;

X is a halogen atom; and
Y is hydroxy or a leaving group;
so obtaining a compound of formula:

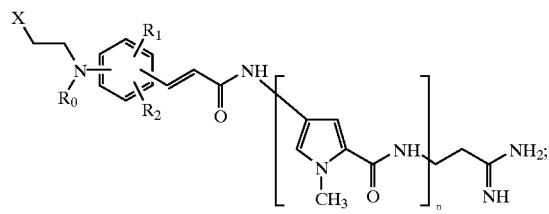

and then, when B is different from

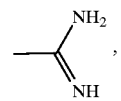

reacting compound (IV) with:

(i) $H_2N$—$(CH_2)_p$—$NH_2$, where p is 2 or 3, so obtaining a compound of formula (I) having B equal to:

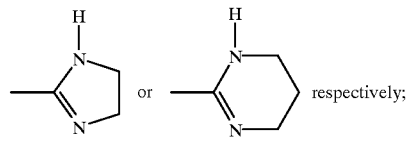

respectively;

(ii) $H_2N$—$CH_2$—$CHO$, so obtaining a compound of formula (I) having B equal to:

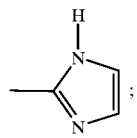

(iii) $H_2N$—$CN$, so obtaining a compound of formula (I) having B equal to:

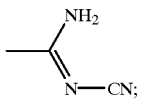

(iv) $H_2N$—$OH$, so obtaining a compound of formula (I) having B equal to:

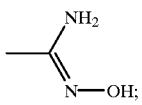

(v) $H_2N$—$NH_2$, so obtaining a compound of formula (I) having B equal to:

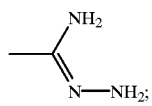

(vi) HNR₄R₅, so obtaining a compound of formula (I) having B equal to:

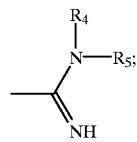

and then optionally with H₂NR₃, so obtaining a compound of formula (I) having B equal to:

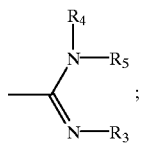

wherein $R_3$, $R_4$, and $R_5$, which may be the same or different, are each hydrogen or $C_1$–$C_4$ alkyl, with the proviso that at least one of $R_3$, $R_4$, and $R_5$ is $C_1$–$C_4$ alkyl;

(vii) succinic anhydride, so obtaining a compound of formula (I) having B equal to —C≡N;

(viii) water in an alkaline medium, so obtaining a compound of formula (I) having B equal to —CO—NR₈R₉ wherein $R_8$ and $R_9$ are both hydrogen;

(ix) HNR₈R₉, so obtaining a compound of formula (I) having B equal to:

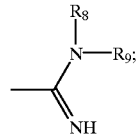

and then with water in an alkaline medium, so obtaining a compound of formula (I) having B equal to —CO—NR₈R₉, wherein $R_8$ and $R_9$, which may be the same or different, are each hydrogen or $C_1$–$C_4$ alkyl;

or:

(b) when B is different from

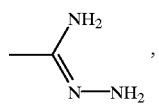

reacting a compound of formula:

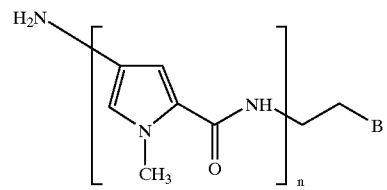

wherein n is 2, 3 or 4; B is selected from:

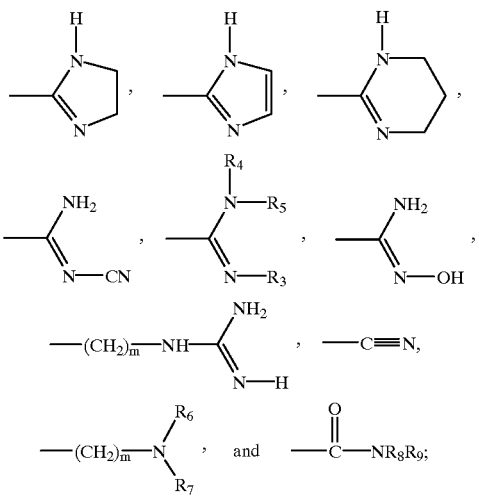

wherein $R_3$, $R_4$, $R_5$, $R_6$, $R_7$, $R_8$ and $R_9$, which may be the same or different, are each hydrogen or $C_1$–$C_4$ alkyl, and m is 0, 1 or 2;

with a compound of formula:

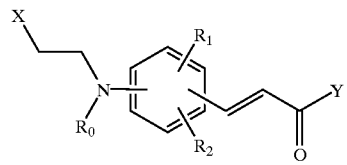

wherein:
$R_0$ is $C_1$–$C_4$ alkyl or $C_1$–$C_3$ haloalkyl;
$R_1$ and $R_2$, which may be the same or different, are each hydrogen, $C_1$–$C_4$ alkyl optionally substituted by one or more fluorine atoms, or $C_1$–$C_4$ alkoxy;
X is a halogen atom; and
Y is hydroxy or a leaving group;
so obtaining the corresponding compound of formula (I).

5. A composition, which comprises a compound as defined in claim 1, as an active principle, in association with one or more acceptable carriers and/or diluents.

6. The composition of claim 5, further comprising an additional antitumor agent.

* * * * *